US00PP19715P2

(12) United States Plant Patent
Yazawa

(10) Patent No.: US PP19,715 P2
(45) Date of Patent: Feb. 17, 2009

(54) ***PETUNIA* PLANT NAMED 'NARUPETU DOUBLE APPLE'**

(50) Latin Name: *Petunia×hybrida*
Varietal Denomination: Narupetu Double Apple

(75) Inventor: Hidenaru Yazawa, Yonago (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/074,408

(22) Filed: Mar. 3, 2008

(51) Int. Cl.
*A01H 5/00* (2006.01)

(52) U.S. Cl. ..... Plt./356
(58) Field of Classification Search ..... Plt./356
See application file for complete search history.

*Primary Examiner*—Kent L Bell
(74) *Attorney, Agent, or Firm*—C. A. Whealy

(57) ABSTRACT

A new and distinct cultivar of *Petunia* plant named 'Narupetu Double Apple', characterized by its trailing plant habit; vigorous growth habit; freely branching and flowering plant habit; long flowering period; medium-sized double red purple-colored flowers; and good garden performance.

1 Drawing Sheet

Botanical designation: *Petunia×hybrida.*
Cultivar denomination: 'Narupetu double apple'.

BACKGROUND OF THE INVENTION

The present invention relates to a new and distinct cultivar of *Petunia,* botanically known as *Petunia×hybrida* and hereinafter referred to by the name 'Narupetu Double Apple'.

The new *Petunia* is a product of a planned breeding program conducted by the Inventor in Yonago, Tottori, Japan. The objective of the breeding program is to create new *Petunia* cultivars with attractive foliage and flower coloration.

The new *Petunia* originated from a cross-pollination made by the Inventor in June, 2002 in Yonago, Tottori, Japan of a proprietary selection of *Petunia×hybrida* identified as code number 02P-R-1, not patented, as the female, or seed, parent with a proprietary selection of *Petunia×hybrida* identified as code number 02P-DW-1, not patented, as the male, or pollen, parent. The new *Petunia* was discovered and selected by the Inventor as a single flowering plant within the progeny of the stated cross-pollination in a controlled environment in Yonago, Tottori, Japan.

Asexual reproduction of the new *Petunia* by terminal cuttings in a controlled environment in Yonago, Tottori, Japan since October, 2004 has shown that the unique features of this new *Petunia* are stable and reproduced true to type in successive generations.

SUMMARY OF THE INVENTION

The cultivar Narupetu Double Apple has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Narupetu Double Apple'. These characteristics in combination distinguish 'Narupetu Double Apple' as a new and distinct cultivar of *Petunia::*

1. Trailing plant habit.
2. Vigorous growth habit.

3. Freely branching and flowering plant habit.
4. Long flowering period.
5. Medium-sized double red purple-colored flowers.
6. Good garden performance.

Plants of the new *Petunia* can be compared to plants of the female parent selection. Plants of the new *Petunia* differ primarily from plants of the female parent selection in flower form as plants of the female parent selection have single flowers.

Plants of the new *Petunia* can be compared to plants of the male parent selection. Plants of the new *Petunia* differ from plants of the male parent selection in the following characteristics:

1. Plants of the new *Petunia* are more trailing than and not as upright as plants of the male parent selection.
2. Plants of the new *Petunia* and the male parent selection differ in flower color as plants of the male parent selection have white-colored flowers.

Plants of the new *Petunia* can also be compared to plants of the cultivar Burietta Rose Vivid Pink, not patented. In side-by-side comparisons conducted in Yonago, Tottori, Japan, plants of the new *Petunia* and the cultivar Burietta Rose Vivid Pink differed in the following characteristics:

1. Plants of the new *Petunia* were shorter, but broader than plants of the cultivar Burietta Rose Vivid Pink.
2. Plants of the new *Petunia* had larger and broader leaves than plants of the cultivar Burietta Rose Vivid Pink.

BRIEF DESCRIPTION OF THE PHOTOGRAPHS

The accompanying colored photographs illustrate the overall appearance of the new *Petunia,* showing the colors as true as it is reasonably possible to obtain in colored reproductions of this type. Colors in the photographs may differ slightly from the color values cited in the detailed botanical description which accurately describe the colors of the new *Petunia.*

The photograph at the top of the sheet comprises a side perspective view of a typical flowering plant of 'Narupetu Double Apple' grown in a container.

The photograph at the bottom of the sheet is a close-up view of a typical plant of 'Narupetu Double Apple'.

DETAILED BOTANICAL DESCRIPTION

The aforementioned photographs and following observations, measurements and values describe plants grown in Higashiomi, Shiga, Japan, under commercial practice during the spring and early summer in an outdoor nursery with average day temperatures of 23° C. and average night temperatures of 13° C. Plants had been growing for about four months when the photographs and description were taken. In the following description, color references are made to The Royal Horticultural Society Colour Chart, 2001 Edition, except where general terms of ordinary dictionary significance are used.

Botanical classification: *Petunia×hybrida* cultivar Narupetu Double Apple.

Parentage:

*Female, or seed, parent.*—Proprietary selection of *Petunia×hybrida* identified as code number 02P-R-1, not patented.

*Male, or pollen, parent.*—Proprietary selection of *Petunia×hybrida* identified as code number 02P-DW-1, not patented.

Propagtion:

*Type.*—By terminal cuttings.

*Time to initiate roots.*—About one week at temperatures of 20° C. to 25°.

*Time to produce a rooted young plant.*—About three weeks at temperatures of 20° C. to 25° C.

*Root description.*—Fine, fibrous; light brown in color.

*Rooting habit.*—Freely branching.

Plant description:

*Plant and growth habit.*—Trailing plant habit. Freely branching with about twelve lateral branches developing per plant; pinching enhances lateral branch development. Vigorous growth habit.

*Plant height.*—About 9.1 cm.

*Plant diameter.*—About 63.8 cm.

Lateral branch description:

*Length.*—About 32.2 cm.

*Diameter.*—About 2.3 mm.

*Internode length.*—About 1 cm.

*Strength.*—Strong.

*Aspect.*—Decumbent.

*Texture.*—Pubescent.

*Color.*—144A.

Foliage description:

*Arrangement.*—Alternate, simple.

*Length.*—About 5.4 cm.

*Width.*—About 2.2 cm.

*Shape.*—Ovate.

*Apex.*—Acute.

*Base.*—Obtuse.

*Margin.*—Entire.

*Texture, upper and lower surfaces.*—Pubescent.

*Venation pattern.*—Pinnate; reticulate.

*Color.*—Developing and fully expanded foliage, upper surface: 137B; venation, 145B. Developing and fully expanded foliage, lower surface: 146B; venation, 145B.

*Petiole.*—Length: About 5.8 mm. Diameter: About 1.2 mm. Texture, upper and lower surfaces: Sparsely pubescent. Color, upper and lower surfaces: 145B.

Flower description:

*Flower arrangement and habit.*—Double flowers arising from leaf axils. Freely flowering habit with usually about 40 open flowers per plant. Flowers persistent. Flowers face mostly outwardly. Flowers not fragrant.

*Natural flowering season.*—Plants of the new *Petunia* initiate and develop flowers about three to four weeks after planting. Long flowering period; flowering commences naturally during the spring and plants flower continuously throughout the summer until late autumn in Japan.

*Flower longevity.*—Individual flowers last about seven to ten days on the plant.

*Flower diameter.*—About 4.7 cm.

*Flower length (depth).*—About 3.4 cm.

*Throat diameter.*—About 1.5 cm.

*Tube diameter, base.*—About 5 mm.

*Tube length.*—About 2.2 cm.

*Flower bud.*—Shape: Cylindrical. Length: About 2.3 cm. Diameter: About 8.2 mm. Color: N81B.

*Corolla.*—Arrangement: About 25 petals in two to three whorls fused at the base and opening into a flared trumpet. Petal length from throat: About 2 cm. Petal width: About 1.8 cm. Petal shape: Spatulate. Petal apex: Acute. Petal margin: Entire; slightly undulate. Petal texture, upper and lower surfaces: Smooth, glabrous; velvety. Tube texture: Sparsely pubescent. Color: Petal, when opening and fully opened, upper surface: Close to N74A; color becoming closer to N78A with subsequent development. Petal, when opening and fully opened, lower surface: Close to N80C. Throat: Close to N80C. Tube: Close to 77B.

*Calyx.*—Arrangement: One star-shaped calyx tube with five sepals fused at the base per flower. Sepal length: About 1.4 cm. Sepal width: About 2.1 mm. Sepal shape: Lanceolate. Sepal apex: Rounded. Sepal margin: Entire. Sepal texture, upper and lower surfaces: Pubescent. Color, upper surface: 137B. Color, lower surface: 144A.

*Peduncles.*—Length: About 2.5 cm. Diameter: About 1 mm. Strength: Strong. Texture: Sparsely pubescent. Color: 144A.

*Reproductive organs.*—Stamens: Quantity/arrangement: Five per flower. Stamen length: About 4 mm to 15 mm. Anther shape: Ellipsoidal. Anther size: About 1 mm by 1 mm. Anther color: 94D. Pollen amount: Scarce. Pollen color: 94C. Pistils: Quantity: One per flower. Pistil length: About 1 cm. Style color: 144D. Stigma shape: Transversely ellipsoidal. Stigma color: 144A. Ovary color: 144A.

*Seed/fruit.*—Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen/pest resistance: Plants of the new *Petunia* have not been observed to be resistant to pests and pathogens common to *Petunia*.

It is claimed:

1. A new and distinct *Petunia* plant named 'Narupetu Double Apple' as illustrated and described.

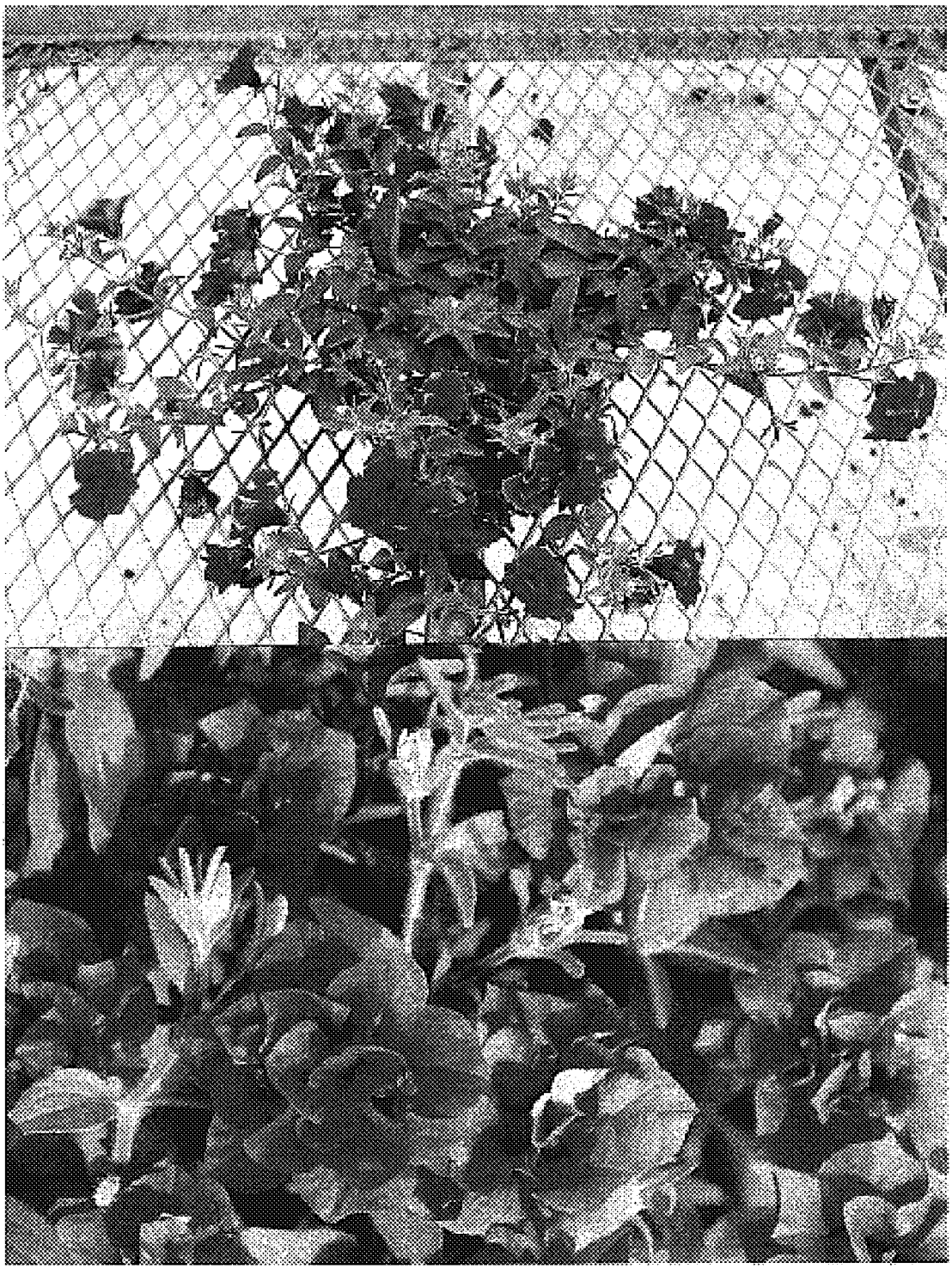

* * * * *